(12) United States Patent
Webber

(10) Patent No.: US 7,064,329 B2
(45) Date of Patent: Jun. 20, 2006

(54) AMPLIFIER-ENHANCED OPTICAL ANALYSIS SYSTEM AND METHOD

(75) Inventor: Michael Evan Webber, Culver City, CA (US)

(73) Assignee: Franalytica, Inc., Santa Monica, CA (US)

( * ) Notice: Subject to any disclaimer, the term of this patent is extended or adjusted under 35 U.S.C. 154(b) by 358 days.

(21) Appl. No.: 10/701,797

(22) Filed: Nov. 4, 2003

(65) Prior Publication Data

US 2004/0094716 A1    May 20, 2004

Related U.S. Application Data

(63) Continuation-in-part of application No. 09/935,011, filed on Aug. 21, 2001, now abandoned.

(51) Int. Cl.
*G01N 21/35* (2006.01)

(52) U.S. Cl. .............................. 250/339.12; 250/341.2; 250/343

(58) Field of Classification Search ........... 250/339.12, 250/339.01, 339.07, 341.7; 356/317, 318, 356/319, 320
See application file for complete search history.

(56) References Cited

U.S. PATENT DOCUMENTS

| | | | | |
|---|---|---|---|---|
| 4,871,916 A | * | 10/1989 | Scott | 250/338.5 |
| 5,616,826 A | * | 4/1997 | Pellaux et al. | 73/24.02 |
| 5,824,884 A | * | 10/1998 | Olender et al. | 73/40.5 A |
| 5,841,797 A | * | 11/1998 | Ventrudo et al. | 372/6 |
| 6,015,969 A | * | 1/2000 | Nathel et al. | 250/227.27 |
| 6,043,504 A | * | 3/2000 | Fujita et al. | 250/573 |
| 6,148,658 A | * | 11/2000 | Chou | 73/24.01 |
| 6,188,705 B1 | * | 2/2001 | Krainak et al. | 372/32 |
| 6,363,772 B1 | * | 4/2002 | Berry | 73/24.02 |
| 6,403,944 B1 | * | 6/2002 | MacKenzie et al. | 250/214.1 |
| 6,437,320 B1 | * | 8/2002 | Yoshida et al. | 250/227.11 |
| 6,552,792 B1 | * | 4/2003 | Pilgrim et al. | 356/432 |
| 2003/0038237 A1 | * | 2/2003 | Webber | 250/339.12 |

* cited by examiner

*Primary Examiner*—Albert Gagliardi
(74) *Attorney, Agent, or Firm*—Jones Day

(57) ABSTRACT

An amplifier-enhanced optical analysis system and method to optically analyze a molecular component of a gas, liquid, or solid. The amplifier-enhanced optical system comprises a laser, a light amplifier, and an optical analysis means, all optically coupled so that light at a predetermined wavelength in the near-infrared spectrum is transported from the laser, through the light amplifier, and to the optical analysis means, wherein the predetermined wavelength corresponds to an absorption feature of the molecular component. Optical analysis means preferably comprises photoacoustic analysis equipment.

21 Claims, 1 Drawing Sheet

AMPLIFIER-ENHANCED OPTICAL ANALYSIS SYSTEM AND METHOD

RELATED APPLICATION

This is a continuation-in-part of patent application Ser. No. 09/935,011 filed Aug. 21, 2001 now abandoned.

BACKGROUND OF THE INVENTION

1. Field of the Invention

The field of the present invention is optical analysis systems, and more particularly, optical analysis systems that utilize light at specific wavelengths to optically analyze the properties of gases, liquids, or solids.

2. Background

Different optical analysis techniques are currently in use to analyze the properties of molecules that are components of gases, liquids, or solids. One of the more common techniques, used frequently in the analysis of gases, is absorption spectroscopy, whereby light having a wavelength that corresponds to an absorption feature of a particular molecule is directed through a gas sample. The power of the emerging light is measured, compared against the power of the light incident at the sample, and used to determine whether the particular molecule is present and if it is present, its concentration. Other optical analysis techniques that utilize optics to analyze the characteristics of a molecular component are, for example, photoacoustic spectroscopy, fluorescence spectroscopy, cavity ring-down spectroscopy, fiber interferometry, evanescent wave spectroscopy, and scattering spectroscopy. These other techniques may be used to determine properties such as the presence and size of the particular molecule, concentration, temperature, etc.

The absorption spectrum of any molecule must be considered to determine which of the wavelengths it absorbs will yield the best results of any given optical analysis. For example, carbon monoxide has absorption bands in the near-infrared and infrared spectrum centered at wavelengths of approximately 1.56 μm, 2.35 μm, and 4.65 μm. The absorption line strengths of carbon monoxide, however, are not uniform within a band, nor are they uniform across these three different bands. For example, the strongest absorption transition at 1.56 μm is approximately 125 times weaker than the strongest absorption transition at 2.35 μm, and approximately 20,000 times weaker than the strongest absorption transition at 4.65 μm. The absorption spectra of other molecules, such as, for example, carbon dioxide and nitric oxide, show similar trends in absorption strength, with absorption strengths being much lower at the shorter wavelengths in the near-infrared spectrum than at the longer wavelengths in the infrared spectrum or in some instances in the UV spectrum.

Absorption spectroscopy benefits tremendously by utilizing a wavelength that overlaps with a high absorption line strength for the species of interest because the sensitivity of absorption spectroscopy measurements is directly proportional to the absorption line strength and the path length of the radiation through the sample being analyzed. Therefore, an absorption spectrometry analysis of carbon monoxide using the longer wavelength can enhance the sensitivity of the measurements by a factor of 20,000 over measurements performed using shorter wavelengths. The difference in absorption line strength for many molecules may vary by a factor of hundreds to tens thousands of times between the shorter and longer wavelengths in the near-infrared and infrared spectrum, with the longer wavelengths generally yielding greater sensitivity in absorption measurements.

Due to the potential for improved sensitivity during the absorption spectroscopy measurement, strategies that have been developed thus far tend to take advantage of the stronger absorption features in the infrared and UV spectrum. However, lasers and other associated equipment that operate at these wavelengths are bulky and expensive. Therefore, the strategies tend to focus not only on increasing sensitivity, but also on portability and affordability.

The present state of the art teaches that the combination of the following three strategies yields the highest sensitivity increase while also enabling portable and affordable absorption spectroscopy. First, because lasers producing near-infrared radiation are readily available and economical, techniques such as non-linear frequency conversion are often used to convert near-infrared radiation into mid-infrared or UV radiation in order to take advantage of stronger absorption features. In addition, because the conversion process is highly inefficient at low values of near infrared radiation power and it results in an extreme loss of power at the converted frequency, fiber amplifiers may be employed in conjunction with the non-linear frequency conversion process. The fiber amplifiers increase the radiation power available to the non-linear conversion process, thereby partially overcoming the inefficiencies of the conversion process. Second, because the detection sensitivity of absorption spectroscopy is directly proportional to path length in the sample, path lengths are sometimes increased through the implementation of multi-pass optical arrangements, including multi-pass cells. Third, sophisticated techniques such as frequency modulation, auto-balancing, etc., may be employed to increase the signal to noise ratio, thereby increasing the overall detection sensitivity.

The above strategy of generating infrared or UV radiation from near-infrared sources, however, does not provide similar advantages for all molecules because not all molecules have absorption spectrum features similar to that of carbon monoxide. Some molecules, such as ammonia and methane, have absorption bands that increase in magnitude comparatively little from the near-infrared to the mid-infrared spectrum. Ammonia has several near-infrared spectral absorption bands at wavelengths of approximately 1.5 μm, 1.65 μm, 2.0 μm, 2.3 μm, and 3.0 μm, with the strongest absorption transition at 3.0 μm being only approximately 8–10 times stronger than the strongest absorption transition at 1.5 μm. Similarly, methane has spectral absorption bands at wavelengths of approximately 1.65 μm and 3.3 μm, with the strongest absorption transition at 3.3 μm being approximately 75 times stronger than the strongest absorption transition at 1.65 μm. Therefore, the advantages gained through the use of mid-infrared radiation to analyze molecules such as carbon monoxide are not as attractive when analyzing molecules such as ammonia and methane.

A second optical analysis technique, photoacoustic spectroscopy, is recognized as being a very sensitive technique. Photoacoustic spectroscopy, however, has also traditionally been implemented with the longer infrared wavelengths because stronger absorption features are typically found in that spectrum and because of the high power lasers available at those wavelengths. For photoacoustic spectroscopy, the available sensitivity is directly proportional to the available laser power. As with absorption spectroscopy, it is desirable to take advantage of commercially available near-infrared lasers to make photoacoustic spectroscopy more affordable and portable, and as a result, previous studies have used near-infrared lasers to generate infrared radiation corresponding to the desired absorption feature using the aforementioned non-linear frequency conversion techniques.

The problem associated with this approach, however, is that photoacoustic sensors would actually lose sensitivity because of the inefficiencies of non-linear frequency conversion, even if a fiber-amplifier were employed to counteract these inefficiencies. Therefore, other techniques have been developed to increase the sensitivity of photoacoustic sensors using near-infrared sources, such as the ones reported in the study by M. Feher et al., *Applied Optics*, 33(9): 1655 (1994). In that study, a diode laser operating in the near-infrared spectrum was used to create a simple, inexpensive, and portable photoacoustic spectrometer to perform an analysis of ammonia. In order to compensate for ammonia's low absorption coefficients near 1532 nm and increase the sensitivity of the analysis, the radiation was frequency modulated and a sophisticated resonant acoustic gas cell was employed. These techniques enhanced the signal and minimized the effects of noise during the analysis. The sophisticated photoacoustic cell and the frequency modulated radiation were credited with increasing the sensitivity of the absorption measurements by two orders of magnitude. Achieving such sensitivity increases without the need to employ a sophisticated photoacoustic cell, however, is desirable.

Improved systems and methods are therefore needed to enhance the sensitivity of optical analyses performed using near-infrared radiation. Such systems and methods should not only have sufficient sensitivity, but also improved simplicity.

SUMMARY OF THE INVENTION

The present invention is directed to an amplifier-enhanced optical analysis system and method. The system and method may be employed to analyze the properties of molecular components in a gas, liquid, or solid. Light at a predetermined wavelength in the near-infrared spectrum is amplified, wherein the amplified light is subsequently maintained at the predetermined wavelength. The amplified light is thereafter utilized for optical analysis of a sample.

Thus, in a first separate aspect of the present invention, a laser emits light at a predetermined wavelength in the near-infrared spectrum that typically corresponds to an absorption feature of the molecular component being analyzed. The laser is optically coupled to a light amplifier, which receives the light. The light amplifier amplifies the light at the predetermined wavelength. Optical analysis means is optically coupled to the light amplifier and receives the amplified light to use in the analysis of the molecular component.

In a second separate aspect of the present invention, optical fibers may optically couple any of the light emitting or light receiving elements.

In a third separate aspect of the present invention, the light amplifier comprises a fiber amplifier.

In a fourth separate aspect of the present invention, the light amplifier comprises a semiconductor optical amplifier.

In a fifth separate aspect of the present invention, the optical analysis means comprises a photoacoustic spectrometer.

In a sixth separate aspect of the invention, multiple species or components may be simultaneously analyzed, a single component may be analyzed at multiple wavelengths or at multiple locations, or light from multiple lasers may be used to enhance the analysis of a single component. A plurality of lasers generate light at one or more predetermined wavelengths in the near-infrared spectrum, wherein each of the predetermined wavelengths corresponds to an absorption feature of the component or components being analyzed. The light from the plurality of lasers is multiplexed into a single optical path and then amplified by a light amplifier. Alternatively, the light from each laser may be amplified before being multiplexed into a single optical path. The amplified light is then received by the optical analysis means and is utilized in analyzing the component or components.

In an eighth separate aspect of the present invention, any of the foregoing aspects may be employed in combination.

Accordingly, it is an object of the present invention to provide an improved system and method for analyzing a molecular component of a gas, liquid, or solid, by amplifying light in the near-infrared spectrum, wherein the wavelength of the light corresponds to an absorption feature of the molecular component, and utilizing the light in spectroscopic analysis of the molecular component. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
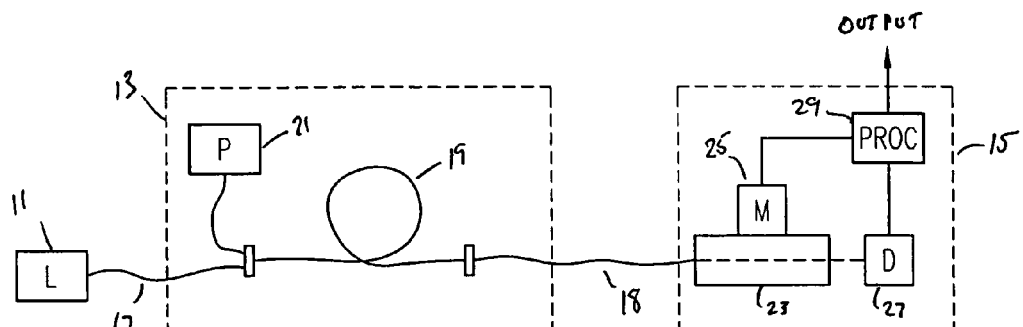
FIG. 1 illustrates a fiber amplifier-enhanced optical analysis system in accordance with a preferred embodiment of the present invention.

Turning in detail to the drawings, FIG. 1 illustrates an amplifier-enhanced optical analysis system in accordance with a preferred embodiment of the present invention. The system of FIG. 1 may be used to analyze a particular molecular component in gases, liquids, or solids using known optical analysis methods such as absorption spectroscopy, photoacoustic spectroscopy, fluorescence spectroscopy, cavity ring-down spectroscopy, fiber interferometry, evanescent wave spectroscopy, and scattering spectroscopy.

The optical analysis system in FIG. 1 comprises a laser 11, a fiber amplifier 13, and optical analysis means 15, which comprises photoacoustic analysis equipment in the present embodiment. The laser 11 is optically coupled to the fiber amplifier 13 and the fiber amplifier 13 is also optically coupled to photoacoustic analysis equipment 15 through optical fibers 17, 18. The laser 11 also preferably includes an isolator to minimize optical feedback from the fiber amplifier 13. Thus, when the laser 11 emits light, the light is transported through the first optical fiber 17 to the fiber amplifier 13 where it is amplified. Amplified light is thereafter transported from the fiber amplifier 13 to the photoacoustic analysis equipment 15 through the second optical fiber 18.

In the preferred embodiment, the predetermined wavelength corresponds to an absorption feature of the molecular component being analyzed. The laser preferably emits either pulsed light or continuous wave light in a narrow band in the near-infrared spectrum centered about the predetermined wavelength. If necessary, depending on the laser used, a feedback loop to the laser control circuitry may be included to stabilize the laser's output at the predetermined wavelength. Alternatively, a laser emitting a wide spectrum of wavelengths may be used if it includes a wavelength selector such as a grating, whether it is a fiber grating, a Bragg reflector, or an external grating, to selectively pass the light at the predetermined wavelength. Other wavelength control and/or selecting mechanisms known in the art may also be employed as desired.

In the preferred embodiment, where light is used to perform photoacoustic analyses of a gas, the light output from the laser 11 is pulsed or modulated in a regular and periodic manner at between approximately 20 and 20,000 cycles per second. The pulsing or modulation may be achieved by modulating the power supply to the laser between an on state and an off state, modulating the power or wavelength with a small amplitude dither at a higher frequency, placing a light chopper between the laser's output and the fiber coupling, or by any other method known in the art. In alternative embodiments, the light may have a fixed wavelength, or it may be scanned through a series of wavelengths, or it may be amplitude or frequency modulated. The particular properties of the light depend on the optical analysis means used and the molecular component or components analyzed.

The optical fibers 17, 18 may be any appropriate type of optical fiber, such as single mode, multi-mode, polarization-maintaining, etc., that transmits the wavelength emitted by the laser. Certain advantages are achieved by using optical fiber to transport the light, as opposed to transporting the light through free space, although the latter may be used where desired. One advantage is found in the convenience of coupling the fibers to the various components of the system. A second advantage is that fiber coupling eliminates the need to have all the components in the nearly perfect optical alignment needed for the light to travel through free space between components. Moreover, fiber coupling allows additional fiber splitters to be implemented for splitting a fraction of the radiation into a separate optical path that can be used for laser line-locking, reference cell measurements, wavelength measurements, etc. with minimal effect on the radiation that is connected to the optical analysis means. Fiber coupling also eliminates the need to provide additional beam shaping optics at transitions the light makes between components. By eliminating such complications, fiber coupling enables different components to be substituted into and out of the system with relative ease. For example, a second laser emitting light at the same wavelength in the near-infrared spectrum may be substituted into the system in the event the first laser fails, or at a second wavelength to perform optical analyses of a second molecular component. The same may also be done with the fiber amplifier and the analysis equipment.

The fiber amplifier 13 in the preferred embodiment includes a doped fiber 19 and a pump laser 21, the operational aspects of which are well known to those skilled in the art. The doped fiber 19 receives the light from the laser and, using power supplied by the pump laser 21, emits amplified light at the predetermined wavelength, wherein the amplified light has the same characteristics as the light input into the amplifier, but at a greater power. Additionally, fiber amplifiers maintain the radiation line-width of the input light during amplification, and thus can be used with narrow line-width lasers for high-resolution measurements.

The type of fiber amplifier used is based on the predetermined wavelength and may be of any type known in the art that amplifies light in the near-infrared spectrum at the predetermined wavelength. The amount of amplified power provided by the fiber amplifier may vary depending on several factors such as the dopant used in the doped-fiber, the length of the doped-fiber, and the power of the pump laser. However, the most desirable results are often achieved using fiber amplifiers that provide more than 100 mW of amplified power. The operative wavelength used in the pump laser is chosen based on the doping type of the doped fiber, the wavelength of the light being amplified, and the particular noise or other characteristics that are appropriate for the particular application. The method of pumping the doped-fiber 19 may include methods such as end pumping, side pumping, co-propagating pumping, bi-directional pumping, Raman fiber laser pumping, etc.

As an alternative to using a laser in combination with a fiber amplifier, as illustrated in FIG. 1, a fiber laser which emits light at the predetermined wavelength in the near-infrared spectrum may be used in place of the two components. A fiber laser, if employed, could be optically coupled directly to the photoacoustic analysis equipment or optically coupled through an optical fiber. Such a substitution could be performed without losing any of the functionality of the present invention. A partial list of dopants which have been found to create operational fiber lasers and fiber amplifiers in silica fiber can be found in *Optical Fibre Lasers and Amplifiers*, p. 162, P. W. France (ed.): CRC Press, Florida, 1991, the disclosure of which is incorporated herein by reference.

The photoacoustic analysis equipment 15 in the preferred embodiment is used to detect the presence of and determine the concentration of a particular molecular component in a gas. The operational aspects of photoacoustic spectrometers are well known to those skilled in the art and are therefore only briefly discussed herein. In FIG. 1, the photoacoustic analysis equipment 15 comprises a photoacoustic gas cell 23, a microphone 25, a detector 27, and a processor 29. The microphone 25 is disposed within the gas cell 23 so that it picks up acoustic fluctuations within the gas cell 23. The detector 27 is disposed on a side of the gas cell 23 to detect the power of the amplified light after the amplified light passes through the gas cell 23. Signal outputs from the microphone 25 and the detector 27 are received by the processor 29 and used to determine the concentration of the molecular component being analyzed.

In brief, when the amplified light passes through the gas cell 23, the molecular component absorbs energy from the light because the wavelength of the light corresponds with an absorption feature of the molecular component. The energy absorption causes slight heating within the gas in the gas cell. The heating occurs at regular and periodic intervals because the amplified light is pulsed or modulated and this periodic heating of the gas generates pressure fluctuations, which propagate within the gas cell 23. These pressure fluctuations are sound waves having a frequency equal to the modulation frequency of the amplified light and an amplitude that is proportional to the absorption line strength of the molecular component and the intensity of the incident light at the wavelength that overlaps with the absorption transition. The microphone 25 detects the sound waves and generates a signal output, the power of which, $S_{AC}$, is measured and recorded by the processor 29. The detector 27 detects the power of the amplified light transmitted through the gas cell 23 and generates a signal output, P, which is measured and recorded by the processor 29.

In the absence of background absorption, concentration of the particular component in the gas is proportioned as set out in the equation below and the accompanying description:

$$\text{Concentration} = \text{constant} * \frac{S_{AC}}{P},$$

where $S_{AC}$ is the amplitude of the generated sound waves, P is the power of the amplified light as measured by the detector and the constant is determined by a calibration procedure or reference cell that uses a sample with a known concentration of the particular component in the gas cell and measuring the signal outputs as described above.

When the above system and process are used to measure the concentration of molecules such as ammonia or methane, a distinct advantage is achieved when the power output of the fiber amplifier is increased. This advantage is derived from the fact that the amplitude of the sound waves in photoacoustic spectroscopy, as can be seen from the above equation, is directly proportional to the power of the light passing through the measurement sample. Therefore, as the power output of the fiber amplifier increases, so does the acoustic signal detected by the microphone.

The sensitivity of the above described system and method may be compared with the aforementioned Feher et al. study, the disclosure of which is incorporated herein by reference, in which photoacoustic spectroscopy and near-infrared radiation were used to analyze ammonia. The Feher et al. study employed a sophisticated photoacoustic cell and frequency modulated radiation at 1532 nm, having a power of 5 mW, to achieve an increase in sensitivity of approximately two orders of magnitude. At 1532 nm, ammonia has an absorption line strength of approximately $2.3 \times 10^{-21}$ cm/molecule. Therefore, if the Feher et al. study was conducted using a non-resonant photoacoustic cell, such as the one described in P. Repond et al., Applied Optics, 35(21): 4065–85 (1996) at FIG. 4(a), the disclosure which is incorporated herein by reference, the sensitivity would be directly proportional to the radiation power times the absorption line strength, or approximately $1.15 \times 10^{-25}$ cm*W/molecule. Therefore, by employing the sophisticated photoacoustic cell, the sensitivity of the Feher et al. study would be approximately $1.15 \times 10^{-23}$ cm*W/molecule. If the above described system and method were employed using a fiber amplifier delivering approximately 500 mW of radiation and the same type of non-resonant photoacoustic cell as described in the Repond et al. study, however, then the sensitivity would be approximately $1.15 \times 10^{-23}$ cm*W/molecule, or the same as achieved in the Feher et al. study. The above described system and method can incorporate the sophisticated resonant acoustic cell used in the Feher et al. study, thereby further increasing the sensitivity by another factor of 100 to $1.15 \times 10^{-21}$ cm*W/molecule. Thus, the above described system and method provides approximately the same sensitivity as that disclosed in the Feher et al. study, but without the sophisticated photoacoustic cell, or it can be used to significantly enhance the sensitivity of the instrument.

Important benefits of the preferred embodiment therefore include the ability of a fiber amplifier to maintain a narrow radiation line-width when amplifying light from the laser, the simplicity of the system as previously described, and the cost-effectiveness because components operating in the near-infrared spectrum are in widespread use in the telecommunications industry.

The benefits of the above described system and method are not limited to photoacoustic spectroscopy. The optical analysis means may also incorporate other known optical analysis techniques, such as absorption spectroscopy, fiber interferometry, evanescent wave spectroscopy, cavity ring-down spectroscopy, fluorescence spectroscopy, scattering spectroscopy, and photothermal deflection spectroscopy, which also gain benefits from the increased power in the near-infrared spectrum. Absorption spectroscopy, such as is described in Sanders et al., Proc. Combustion Institute, 28: 587–94 (2000), the disclosure of which is incorporated herein by reference, benefits from input radiation at higher powers in the near-infrared spectrum when used in sooty or dirty environments. Under such conditions, the higher power results in higher throughput of the light to the detector. Additionally, when multi-pass cells are used for absorption spectroscopy, the optical throughput tends to be a small fraction of the input power. Thus, for absorption spectroscopy, higher input powers results in higher throughput, which in turn simplifies signal detection.

Fiber-optic sensors using fiber interferometry or evanescent wave spectroscopy to detect gases, such as are described in Lee et al., Optics Letters, 14(21): 1225–27 (1989) and Klimcak et al., Proc. of the SPIE, 2367: 80–85 (1995), respectively, the disclosures of which are incorporated herein by reference, benefit from input radiation at higher powers in the near-infrared spectrum because the higher power enables the light to be transmitted along greater lengths of fiber, a feature that directly enhances sensitivity.

Cavity ring-down spectroscopy, such as is described in Berden et al., Int. Reviews in Physical Chemistry, 19(4): 565–607 (2000), the disclosure of which is incorporated herein by reference, benefits from input radiation at higher powers in the near-infrared spectrum by enabling the ring-down events to be monitored for longer time periods, thereby yielding more sensitive results, and simplified optical alignments.

Fluorescence spectroscopy (also known as laser-induced fluorescence (LIF) and planar LIF (PLIF)), such as is described in Stanford University course materials, Professor R. K. Hanson, ME 264: Introduction to Spectroscopic Diagnostics for Gases, pp. 155–184, Winter 2000 term, the disclosure of which is incorporated herein by reference, benefits from input radiation at higher powers in the near-infrared spectrum because the signal detected from fluorescing molecules is directly related to the number of photons, or the power of the light, being directed into the medium being analyzed. Thus, increasing the power of the light used directly results in increased signal strength.

Scattering spectroscopy techniques, including Rayleigh scattering and Raman scattering, such as is described in Stanford University course materials, Professor R. K. Hanson, ME 264: Introduction to Spectroscopic Diagnostics for Gases, pp. 75–86, Winter 2000 term, the disclosure of which is incorporated herein by reference, or mie scattering, such as is described in Alan C. Eckbreth, Laser Diagnostics for Combustion Temperature and Species, 2nd ed., pp. 15, 186, and 268, Gordon & Breach, (1988), the disclosure of which is incorporated herein by reference, benefit from input radiation at higher powers in the near-infrared spectrum because higher power in the input radiation yields greater scattered signal and thereby simplified detection, or more sensitive detection.

Photothermal deflection, such as is described in H. S. M. de Vries et al., Atmospheric Environment, 29(10):1069–74 (1995), and H. S. M. de Vries et al., Rev. Sci. Instrum., 66(9): 4655–64 (1995), the disclosures of which are incorporated herein by reference, also benefits from input radiation at higher powers in the near-infrared spectrum because higher power in the input radiation yields greater deflection in the cross-beam. Greater deflection in the cross-beam makes the actual deflection amount easier to detect and increases sensitivity of the measurement.

Figure 2:
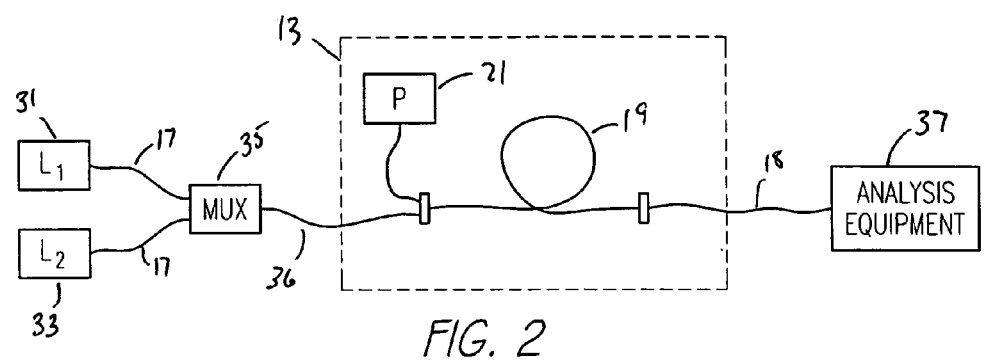
FIG. 2 illustrates a fiber amplifier-enhanced optical analysis system in accordance with a first alternative embodiment of the present invention.
Figure 3:
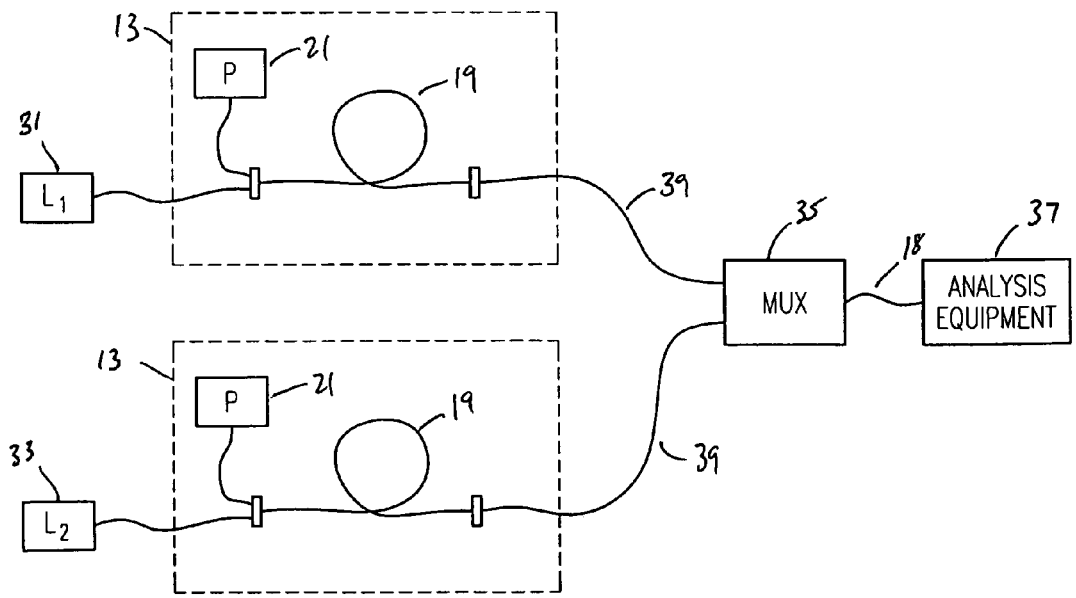
FIG. 3 illustrates a fiber amplifier-enhanced optical analysis system in accordance with a second alternative embodiment of the present invention.

FIGS. 2 and 3 illustrate alternative embodiments of the present invention which may be employed to perform optical analyses on one or more molecules. In FIG. 2, a first laser 31 and a second laser 33 emit light in the near-infrared spectrum at one or more predetermined wavelengths. The light from the two lasers may each correspond to the same absorption feature of a particular molecule, or they may correspond to two different absorption features of a particular molecule, or each may correspond to an absorption feature of a different molecule, or one may correspond to a non-resonant wavelength that is not absorbed by any molecules in the measurement sample. In the system illustrated in FIG. 2, the light from each laser is fiber coupled to a multiplexer 35 which combines the light into a single optical fiber 36 which transports the combined light to the fiber amplifier 13. The fiber amplifier 13 emits amplified light in the manner described above, and the amplified light is transported by an optical fiber 18 to the optical analysis equipment 37 which may comprise any of the aforementioned optical analysis techniques. In this system, because a single fiber amplifier 13 is employed, the light from each laser must have a wavelength within the operational range of the fiber amplifier 13. If the wavelengths are not both within the operational range of the fiber amplifier 13, then the system illustrated in FIG. 3 may be employed. In the system illustrated in FIG. 3, light from each laser 31, 33 is amplified prior to being coupled, by optical fibers 39, to the multiplexer 35 which combines the light into a single optical path. Systems may also be employed having more than two lasers and having as many fiber amplifiers and multiplexers as are needed.

Thus, an amplifier-enhanced optical analysis system and method have been disclosed. While embodiments of the system and method have been described, it would be apparent to those skilled in the art that many more modifications and combinations are possible without departing from the inventive concepts herein. The invention, therefore, is not to be restricted except in the spirit of the following claims.

What is claimed is:

1. An optical analysis system for analyzing a molecular component in a gas, liquid, or solid, the system comprising:
 a laser emitting light at a predetermined wavelength in the near-infrared spectrum which corresponds to an absorption feature of the molecular component being analyzed;
 a fiber amplifier optically coupled to and receiving the light from the laser, wherein the light amplifier emits amplified light at the predetermined wavelength; and
 optical analysis means optically coupled to and receiving the amplified light from the fiber amplifier.

2. The system of claim 1 further comprising an optical fiber disposed between and optically coupling the laser and the fiber amplifier.

3. The system of claim 1 further comprising an optical fiber disposed between and optically coupling the fiber amplifier and the optical analysis means.

4. An optical analysis system for analyzing one or more molecular components in a gas, liquid, or solid, the system comprising:
 a plurality of lasers emitting light at one or more predetermined wavelengths in the near-infrared spectrum, wherein each of the predetermined wavelengths corresponds to an absorption feature of the one or more molecular components being analyzed;
 a multiplexer optically coupled to and receiving the light from the plurality of lasers, wherein the multiplexer combines the light from the plurality of lasers and emits the light into a single optical path;
 a fiber amplifier optically coupled to and receiving the light from the single optical path, wherein the light amplifier emits amplified light at the one or more predetermined wavelengths; and
 optical analysis means optically coupled to and receiving the amplified light from the fiber amplifier.

5. The system of claim 4 further comprising a plurality of optical fibers disposed between and optically coupling the plurality of lasers and the multiplexer.

6. The system of claim 4 further comprising an optical fiber disposed between and optically coupling the multiplexer and the fiber amplifier.

7. The system of claim 4 further comprising an optical fiber disposed between and optically coupling the fiber amplifier and the optical analysis means.

8. An optical gas analysis system for analyzing a molecular component in a gas comprising:
 a laser emitting light at a predetermined wavelength in the near-infrared spectrum which corresponds to an absorption feature of the molecular component being analyzed;
 a fiber amplifier optically coupled to the laser using a first optical fiber, wherein the fiber amplifier receives the light and emits amplified light at the predetermined wavelength in the near-infrared spectrum which corresponds to an absorption feature of the molecular component being analyzed; and
 photoacoustic analysis equipment optically coupled to the fiber amplifier using a second optical fiber, wherein the photoacoustic analysis equipment receives and utilizes the amplified light at the predetermined wavelength to perform analyses of the molecular component.

9. The system of claim 8, wherein the fiber amplifier comprises a rare-earth-doped fiber amplifier.

10. An optical analysis system for analyzing a molecular component in a gas comprising:
 a fiber laser emitting amplified light at a predetermined wavelength in the near-infrared spectrum which corresponds to an absorption feature of the molecular component being analyzed; and
 optical analysis means optically coupled to the fiber laser using an optical fiber, wherein the optical analysis means receives and utilizes the amplified light at the predetermined wavelength to perform analyses of the molecular component.

11. The system of claim 10, wherein the optical analysis means comprises a photoacoustic spectrometer.

12. A method of optically analyzing a molecular component in a gas, liquid, or solid, the method comprising:
 generating, from a laser, light at a predetermined wavelength in the near-infrared spectrum which corresponds to an absorption feature of the molecular component being analyzed;
 receiving the light at a fiber amplifier;
 generating, from the fiber amplifier, amplified light at the predetermined wavelength;
 receiving the amplified light at optical analysis means; and
 analyzing, with the optical analysis means, the molecular component using the amplified light.

13. The method of claim 12, wherein receiving the light at the fiber amplifier includes guiding the light through an optical fiber from the laser to the light amplifier.

14. The method of claim 12, wherein receiving the light at the optical analysis means includes guiding the light through an optical fiber from the fiber amplifier to the optical analysis means.

15. A method of optically analyzing molecular components in a gas, liquid, or solid, the method comprising:
generating, from a plurality of lasers, light at one or more predetermined wavelengths in the near-infrared spectrum, wherein each of the predetermined wavelengths corresponds to an absorption feature of the one or more molecular components being analyzed;
receiving the light at a multiplexer;
combining the light from the plurality of lasers into a single optical path;
receiving the light from the single optical path with a fiber amplifier;
generating, from the fiber amplifier, amplified light at the one or more predetermined wavelengths;
receiving the amplified light at optical analysis means; and
analyzing, with the optical analysis means, the molecular component using the amplified light.

16. The method of claim 15, wherein receiving the light at the fiber amplifier includes guiding the light through an optical fiber from the plurality of lasers to the light amplifier.

17. The method of claim 15, wherein receiving the light at the optical analysis means includes guiding the light through an optical fiber from the fiber amplifier to the optical analysis means.

18. A method of optically analyzing a molecular component in a gas comprising:
generating, from a laser, light at a predetermined wavelength in the near-infrared spectrum which corresponds to an absorption feature of the molecular component being analyzed;
guiding the light through a first optical fiber to a fiber amplifier;
generating, from the fiber amplifier, amplified light at the predetermined wavelength;
guiding the amplified light through a second optical fiber to photoacoustic analysis equipment; and
analyzing, with the photoacoustic analysis equipment, the molecular component using the amplified light.

19. The method of claim 18, wherein the fiber amplifier comprises a rare-earth-doped fiber amplifier.

20. A method of optically analyzing a molecular component in a gas comprising:
generating, from a fiber laser, amplified light at a predetermined wavelength in the near-infrared spectrum which corresponds to an absorption feature of the molecular component being analyzed;
guiding the amplified light through an optical fiber to optical analysis means; and
analyzing, with the optical analysis means, the molecular component using the amplified light.

21. The method of claim 20, wherein the optical analysis means comprises a photoacoustic spectrometer.

* * * * *